(12) United States Patent
Boutinon et al.

(10) Patent No.: US 10,278,573 B2
(45) Date of Patent: May 7, 2019

(54) CORRECTIVE EYEGLASSES AND METHOD FOR SUBJECTIVE REFRACTION BY A WEARER OF SAID EYEGLASSES

(71) Applicant: ESSILOR INTERNATIONAL (COMPAGNIE GENERALE D'OPTIQUE), Charenton-le-Pont (FR)

(72) Inventors: Stephane Boutinon, Charenton-le-Pont (FR); Vincent Tejedor Del Rio, Charenton-le-Pont (FR); Michel Nauche, Charenton-le-Pont (FR)

(73) Assignee: ESSILOR INTERNATIONAL, Charenton-le-Pont (FR)

( * ) Notice: Subject to any disclaimer, the term of this patent is extended or adjusted under 35 U.S.C. 154(b) by 0 days.

(21) Appl. No.: 15/302,669

(22) PCT Filed: Apr. 7, 2015

(86) PCT No.: PCT/FR2015/050890
§ 371 (c)(1),
(2) Date: Oct. 7, 2016

(87) PCT Pub. No.: WO2015/155456
PCT Pub. Date: Oct. 15, 2015

(65) Prior Publication Data
US 2017/0035289 A1 Feb. 9, 2017

(30) Foreign Application Priority Data
Apr. 8, 2014 (FR) ...................................... 14 53130

(51) Int. Cl.
*A61B 3/04* (2006.01)
*A61B 3/00* (2006.01)
(Continued)

(52) U.S. Cl.
CPC .............. *A61B 3/04* (2013.01); *A61B 3/0025* (2013.01); *A61B 3/0033* (2013.01); *A61B 3/028* (2013.01);
(Continued)

(58) Field of Classification Search
CPC ......... A61B 3/036; A61B 3/04; A61B 3/0025; A61B 3/0033; A61B 3/028
(Continued)

(56) References Cited

U.S. PATENT DOCUMENTS

| 3,880,502 A | 4/1975 | Humphrey |
| 5,104,214 A | 4/1992 | Sims |

(Continued)

FOREIGN PATENT DOCUMENTS

| CN | 101094605 A | 12/2007 |
| EP | 1 138 253 | 10/2001 |

(Continued)

OTHER PUBLICATIONS

Chinese Office Action issued in Application No. 201510161980.8, dated Oct. 28, 2016 with English translation.
(Continued)

*Primary Examiner* — Kristina M Deherrera
(74) *Attorney, Agent, or Firm* — Young & Thompson (57) ABSTRACT

The invention relates to vision compensating spectacles comprising means of support (130, 140, 152) on a wearer's face and at least one optical subassembly (110, 120) mounted on the support means (130, 140, 152) opposite at least one of the wearer's eyes.
The optical subassembly (110, 120) comprises three optical elements mounted on the support means in series along an optical axis: a first optical element of cylindrical power for a direction of gaze of the wearer along the optical axis, a second optical element of cylindrical power for the said
(Continued)

direction of gaze and a third optical element of variable spherical power for the said direction of gaze.

The first optical element and the second optical element are adjustable in rotation about the optical axis independently of one another.

15 Claims, 3 Drawing Sheets

(51) Int. Cl.
    *A61B 3/028*     (2006.01)
    *G02C 13/00*     (2006.01)
    *G02B 7/02*     (2006.01)
    *G02B 7/12*     (2006.01)

(52) U.S. Cl.
    CPC .............. *G02B 7/023* (2013.01); *G02B 7/12* (2013.01); *G02C 13/003* (2013.01)

(58) Field of Classification Search
    USPC ....... 351/222, 233, 229, 235, 246, 227, 228, 351/118
    See application file for complete search history.

(56) References Cited

U.S. PATENT DOCUMENTS

| | | | | |
|---|---|---|---|---|
| 7,159,984 B2* | 1/2007 | Fukuma | ................. | A61B 3/04 351/222 |
| 7,959,287 B1* | 6/2011 | Saffra | ................. | G02C 13/003 351/204 |
| 2003/0081175 A1* | 5/2003 | Hosoi | ................. | A61B 3/04 351/222 |
| 2003/0174282 A1 | 9/2003 | Itagaki | | |
| 2003/0231293 A1* | 12/2003 | Blum | ................. | G02B 27/017 356/5.01 |
| 2004/0032567 A1 | 2/2004 | Fukuma et al. | | |
| 2004/0032568 A1 | 2/2004 | Fukuma et al. | | |
| 2013/0173029 A1 | 7/2013 | Caldeira et al. | | |

FOREIGN PATENT DOCUMENTS

| | | |
|---|---|---|
| EP | 1 250 883 A2 | 10/2002 |
| EP | 1 308 123 A2 | 5/2003 |
| EP | 1 433 415 | 6/2004 |
| EP | 2 034 338 A1 | 3/2009 |
| GB | 2 017 966 A | 10/1979 |
| JP | 2000-2857 A | 1/2000 |
| JP | 2003-135397 | 5/2003 |
| JP | 2004-000657 | 1/2004 |
| JP | 2004-073626 | 3/2004 |
| JP | 2007-097707 | 4/2007 |
| JP | 2007-125125 A | 5/2007 |

OTHER PUBLICATIONS

International Search Report, dated Jun. 19, 2015, from corresponding PCT Application.

Japanese Office Action for Application No. 2016-561818, dated Dec. 12, 2018, with English translation provided.

\* cited by examiner

CORRECTIVE EYEGLASSES AND METHOD FOR SUBJECTIVE REFRACTION BY A WEARER OF SAID EYEGLASSES

TECHNICAL FIELD OF THE INVENTION

The present invention relates to the field of optometry.

It relates more particularly to vision compensating spectacles, for example trial spectacles, as well as to a method of subjective refraction of an individual wearing these spectacles.

PRIOR ART

In the context of the measurement of the visual acuity of a patient, it has already been proposed to simulate the visual compensation to be provided, for example by means of trial frames or a refractor such as a refraction head.

In the refraction head, trial lenses are placed on a plurality of discs that are rotated manually or using a motorized mechanism. However, it will be understood that such an object has a substantial bulk and weight related to the number of lenses placed on each disc.

Trial spectacles are less bulky. Provision is indeed made for them to successively receive trial lenses having different corrections, until the correction which is appropriate for the patient is found.

This solution is however rather impractical, particularly because it requires separate storage of the trial lenses in dedicated boxes. It furthermore involves lens changes, resulting in undesired and non-continuous transitions in corrective power.

SUBJECT OF THE INVENTION

In this context, the present invention proposes vision compensating spectacles comprising means of support on a wearer's face and at least one optical subassembly mounted on the support means opposite at least one of the wearer's eyes, characterized in that the optical subassembly comprises three optical elements mounted on the support means in series along an optical axis, including a first optical element of cylindrical power for a direction of gaze of the wearer along the optical axis, a second optical element of cylindrical power for the said direction of gaze and a third optical element of variable spherical power for the said direction of gaze, the first optical element and the second optical element being adjustable in rotation about the optical axis independently of one another.

It is thus possible to obtain a large variety of corrections on spectacles: indeed, by the proposed combination of the three aforementioned optical elements, it is possible to vary the spherical power, the cylindrical power and the cylinder angle that are generated by the optical subassembly.

In the embodiment described, the optical axis is perpendicular to the cylinder axis of the first and second optical elements and the first and second optical elements do not exert any spherical power for the said direction of gaze of the wearer.

Provision is for example made for each of the first, second and third optical elements to be a lens of diameter greater than or equal to 20 mm, thereby making it possible to obtain an optical subassembly having a sufficient size to easily place an eye opposite.

The optical subassembly comprises for example an electronic card designed to control the spherical power of the third optical element, the position of the first optical element about the optical axis and the position of the second optical element in rotation about the optical axis as a function of setpoint information.

Provision may be made moreover for the optical subassembly to comprise an inclinometer and/or a telemeter; the electronic card can then determine the setpoint information as a function particularly of an item of inclination information received from the inclinometer and/or the telemeter.

It is also possible to envisage using a button actuatable by the wearer, so that the electronic card can modify the spherical power of the third optical element should the button be pressed.

Provision may furthermore be made for a reception module designed to receive the setpoint information through a wireless link. The presence of wires which would encumber the wearer of the spectacles is thus avoided. The wearer can therefore have a natural posture when wearing the vision compensating spectacles.

The support means comprise for example a nasal support. The optical subassembly can moreover be mounted on a frame element, optionally in a manner which is adjustable along a horizontal axis.

The nasal support can for its part be mounted adjustable on the frame element.

The support means can furthermore comprise at least one branch of adjustable length.

The spectacles can also comprise an energy (for example electrical) storage system making it possible to energize (electrically) means designed to adjust the spherical power of the third optical element and/or the position of the first optical element about the optical axis and/or the position of the second optical element in rotation about the optical axis, so as to render the apparatus autonomous.

The invention also proposes a method of subjective refraction of an individual wearing spectacles as proposed hereinabove and comprising the following steps:

determination of a type of vision (near vision, intermediate vision or far vision) by use of the inclinometer or the telemeter;

determination, by the electronic card, of at least one item of setpoint information associated with the determined type of vision;

tailoring of the optical power of the third optical element, of the position of the first optical element or of the position of the second optical element as a function of the determined item of setpoint information. To determine the type of vision, use is made for example of the sighting distance (distance of the object gazed at along the line of gaze) determined by virtue of the inclinometer or by virtue of the telemeter; spans of values of the sighting distance are associated with the various types of vision.

Such a method can also comprise the following steps:
detection of the pressing of the button;
tailoring of the optical power as a function of the data received from the control card.

DETAILED DESCRIPTION OF AN EXAMPLE EMBODIMENT

The following description, given with regard to the appended drawings and by way of nonlimiting example, will allow what the invention consists of and how it can be carried out to be well understood.

Figures 1, 2, 5:
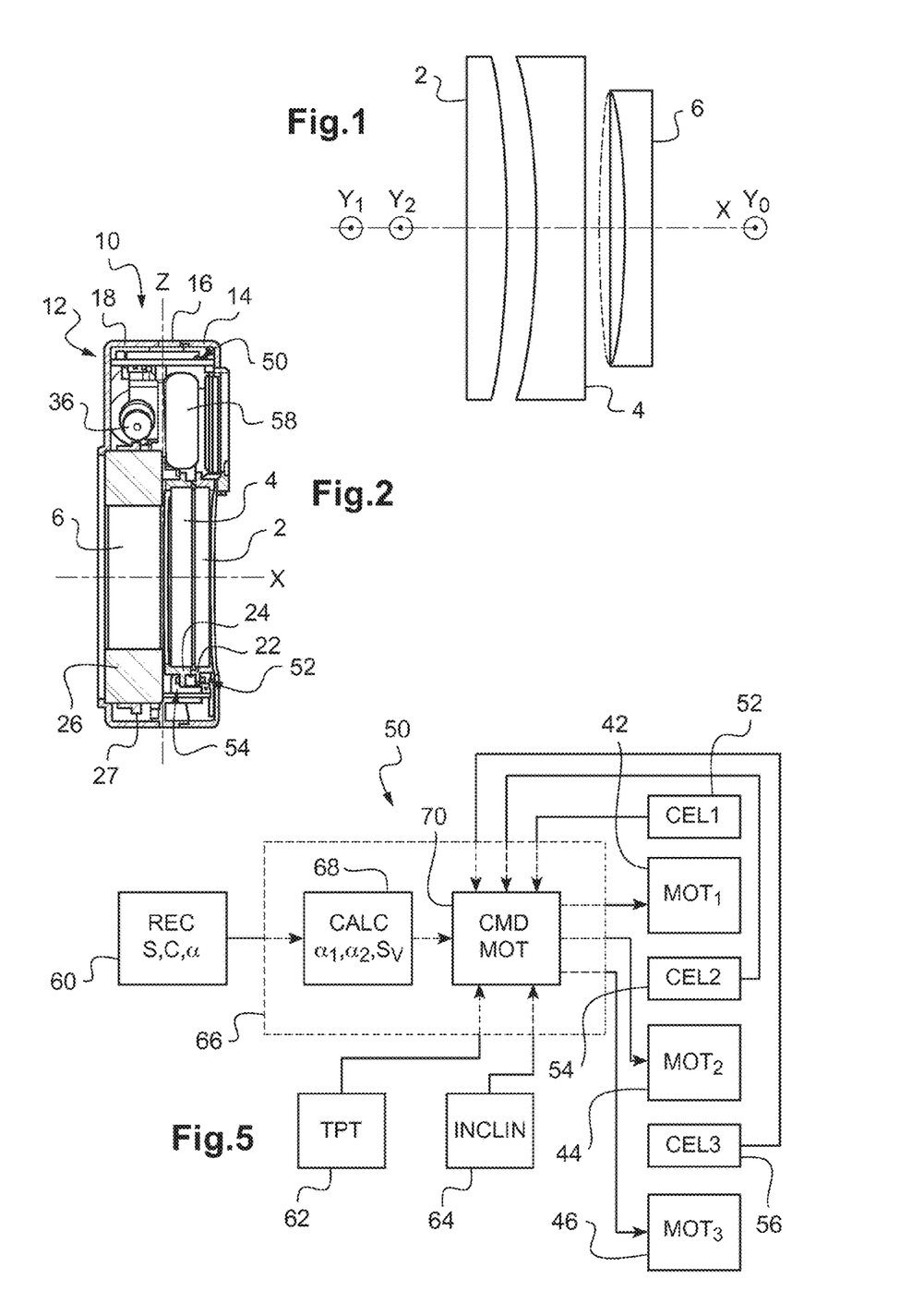
FIG. 1 schematically shows the optical elements used in one example implementation of the invention.
FIG. 2 shows a cross-sectional view of an example vision compensating device that may be used in the context of the invention.
FIG. 5 schematically shows an element for controlling the vision compensating device in FIG. 2.

In FIG. 1 are schematically represented the main optical elements of an exemplary visual compensation device used, as described further on, in vision compensating spectacles in accordance with the teachings of the invention.

These optical elements comprise a convex planar-cylindrical lens 2, of cylindrical power $C_0$, a concave planar-cylindrical lens 4, of negative cylindrical power $-C_0$, and a lens 6 of variable spherical power $S_V$.

The absolute value (or modulus), here $C_0$, of the cylindrical power (here $-C_0$) of the concave planar-cylindrical lens 4 is therefore equal to the absolute value ($C_0$) (or modulus) of the cylindrical power ($C_0$) of the convex planar-cylindrical lens 2.

As a variant, provision could be made for the respective cylindrical powers of the concave planar-cylindrical lens 4 and the convex planar-cylindrical lens 2 to be (slightly) different in absolute value, but they are in any case such that the resulting cylindrical power generated by combining these two lenses has a negligible value (for example smaller than 0.1 dioptres in absolute value) in at least one relative position of these two lenses.

The three lenses 2, 4, 6 are placed on the same optical axis X. Specifically, each of the three lenses 2, 4, 6 has a generally cylindrical exterior shape centred on the optical axis X. In the example described here, the lenses 2, 4, 6 have the following diameters (quantifying their bulk), respectively: 25 mm, 25 mm, 20 mm.

Thus, it will be noted that it is preferable to use this vision compensating device 10 with the eye of the patient located on the side of the variable spherical power lens 6 so that the lenses 2, 4 of cylindrical power, which are larger in diameter, do not limit the field of view defined by the variable spherical power lens 6, which itself is perceived as wide due to its proximity to the eye of the patient.

Each of the three lenses 2, 4, 6 comprises a first planar face, perpendicular to the optical axis X, and a second face opposite the first face and optically active:

the optically active face of the lens 2 is cylindrically convex in shape (the axis $Y_1$ of the cylinder defining this face lying perpendicular to the optical axis X);

the optically active face of the lens 4 is cylindrically concave in shape (the axis $Y_2$ of the cylinder defining this face lying perpendicular to the optical axis X); and the optically active face of the lens 6 of variable spherical power $S_V$ is deformable and may thus adopt a convex spherical shape (as illustrated by the dotted line in FIG. 1), a planar shape or a concave spherical shape (as illustrated by the solid line).

The lens 6 of variable spherical power $S_V$ is for example a lens of the type described in document EP 2 034 338. Such a lens comprises a cavity closed by a transparent deformable membrane and a planar movable transparent wall; the cavity contains a transparent liquid of constant volume that is constrained, to a greater or lesser degree, by the movable face, in order to deform the membrane that is thus either a spherical concave surface, or a planar surface, or a spherical convex surface. In the lens used, a transmission made up of a nut/bolt system ensures transformation of rotary and linear motion. In the example described here, the lens 6 has a variable focal length of between −40 mm and 40 mm, i.e. a variable spherical power $S_V$ of between −25 D and 25 D (D being the dioptre, the unit for measuring vergence, inverse to the focal length expressed in meters).

Moreover, the planar-cylindrical lenses 2, 4 have respectively as already indicated a cylindrical power of $-C_0$ and $C_0$, here with $C_0=5$ D.

As explained in greater detail below, the concave planar-cylindrical lens 4 and the convex planar-cylindrical lens 2 are rotatably mounted about the axis X (rotation centred on the axis X).

The axis $Y_1$ of the convex cylinder formed on the optically active face of the convex planar-cylindrical lens 2 may thus make a variable angle $\alpha_1$ with a reference axis $Y_0$ (which is fixed and perpendicular to the optical axis X).

Likewise, the axis $Y_2$ of the concave cylinder formed on the optically active face of the concave planar-cylindrical lens 4 may make a variable angle $\alpha_2$ with the reference angle $Y_0$.

By calculating refractive power on the various meridians, the following formulae are obtained for the spherical power S, the cylindrical power C and the angle of astigmatism $\alpha$ of the optical subassembly formed from the three optical elements 2, 4, 6 just described:

$$\tan 2\alpha = \frac{\sin 2\alpha_2 - \sin 2\alpha_1}{\cos 2\alpha_2 - \cos 2\alpha_1} = -\frac{\cos(\alpha_1 + \alpha_2)}{\sin(\alpha_1 + \alpha_2)} \quad \text{(formula 1)}$$

$$C = C_0(\cos 2(\alpha - \alpha_2) - \cos 2(\alpha - \alpha_1)) \quad \text{(formula 2)}$$

$$S = S_V - \frac{C}{2}. \quad \text{(formula 3)}$$

It will be noted that the term ($-C/2$) in formula 3 corresponds to a spherical power generated by the resultant of the 2 lenses providing cylindrical power.

By controlling the rotational position of the convex planar-cylindrical lens 2 and the rotational position of the concave planar-cylindrical lens 4, independently of one another, as described hereinafter, it is possible to independently vary each of the angles $\alpha_1$, $\alpha_2$ from 0° to 360° and thus obtain an adjustable cylindrical power C of between $-2.C_0$ and $2.C_0$ (i.e. here between −10 D and 10 D), and for any angle of astigmatism adjustable between 0° and 360° obtained by simultaneous control of the two lenses. As formula 3 indicates, the spherical power resulting from the resultant of the orientation of the 2 cylindrical lenses is compensated for using the lens of variable spherical power.

Moreover, by varying the spherical power $S_V$ of the spherical lens 6, it is possible to adjust the spherical power S of the subassembly formed from the three lenses 2, 4, 6.

According to one envisionable variant, the lenses providing a set cylindrical power could have the same (positive or negative) cylindrical power $C_0$: it could be a question of two, optionally identical, convex planar-cylindrical lenses or, as an alternative, of two, optionally identical, concave planar-cylindrical lenses.

Specifically, in this case, the spherical power S, the cylindrical power C and the angle of astigmatism α of the subassembly formed from these two lenses and from a lens providing variable spherical power are given by the following formulae:

$$\tan 2\alpha = \frac{\sin 2\alpha_2 + \sin 2\alpha_1}{\cos 2\alpha_2 + \cos 2\alpha_1} \qquad \text{(formula 4)}$$

$$C = C_0(\cos 2(\alpha - \alpha_2) + \cos 2(\alpha - \alpha_1)) \qquad \text{(formula 5)}$$

$$S = S_V + C_0 - \frac{C}{2}. \qquad \text{(formula 6)}$$

The term $C_0$-C/2 corresponds to the spherical power induced by the combination of the two lenses providing cylindrical power.

It is therefore also possible in this case to adjust the spherical power S, the cylindrical power C and the angle of astigmatism α, in particular so that the cylindrical power C is zero, by rotating the lenses providing cylindrical power (independently of each other) and by varying the spherical power of the lens providing variable spherical power.

An example vision compensating device 10 that uses the optical elements that have just been described is shown in FIG. 2.

Sometimes in the following description, in order to clarify the explanation, terms such as "upper" or "lower" will be used, which define an orientation in FIGS. 2, 3 and 4. It will be understood that this orientation is not necessarily applicable to the use that will possibly be made of the described device, in particular the use shown in FIGS. 6 to 8.

The vision compensating device 10 comprises a casing 12 formed from a first portion 14, a second portion 16 and a third portion 18, which are placed in succession along the optical axis X and assembled pairwise in planes perpendicular to the optical axis X.

A first toothed wheel 22 is rotatably mounted centred on the optical axis X in the first portion 14 of the casing 12 and bears, at its centre, in an aperture provided for this purpose, the convex planar-cylindrical lens 2. The first toothed wheel 22 and the convex planar-cylindrical lens 2 are coaxial; in other words, in cross section in a plane perpendicular to the optical axis X, the exterior circumference of the first toothed wheel 22 and the circumference of the convex planar-cylindrical lens 2 form concentric circles centred on the optical axis X.

Likewise, a second toothed wheel 24 is rotatably mounted centred on the optical axis X in the second portion 16 of the casing 12 and bears, at its centre, in an aperture provided for this purpose, the concave planar-cylindrical lens 4. The second toothed wheel 24 and the concave planar-cylindrical lens 4 are coaxial; in other words, in cross section in a plane perpendicular to the optical axis X, the exterior circumference of the second toothed wheel 24 and the circumference of the concave planar-cylindrical lens 4 form concentric circles centred on the optical axis X.

A third toothed wheel 27 is rotatably mounted centred on the optical axis X in the third portion 18 of the casing 12. The third toothed wheel 27 is secured to a ring provided on the circumference of a casing 26 which carries the variable spherical power lens 6 and allowing control of the spherical power $S_V$. The casing 26 of the lens 6 of variable spherical power is mounted in the third portion 18 of the casing 12.

Figure 3:
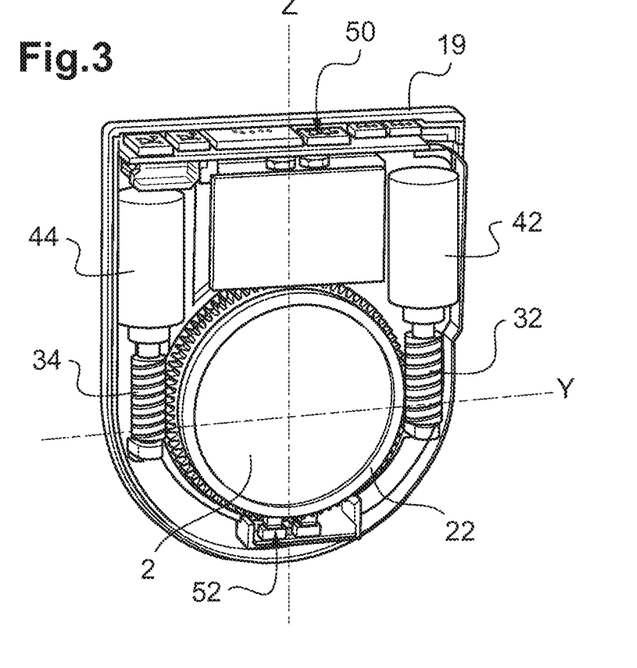
FIG. 3 shows a cutaway view of the vision compensating device in FIG. 2, on the cylindrical lens side.

As may be clearly seen in FIG. 3, the first toothed wheel 22 is rotated (about the optical axis X) by means of a first motor 42 a drive axis of which bears a first grub screw 32 that engages with the first toothed wheel 22. The first motor 42 is for example mounted in the first portion 14 of the casing 12.

The current position of the first toothed wheel 22 is monitored by a first optical cell 52.

Likewise, the second toothed wheel 24 is rotated about the optical axis X by means of a second motor 44 a drive axis of which bears a second grub screw 34 that engages with the second toothed wheel 24. The second motor 44 is for example mounted in the second portion 16 of the casing 12.

The current position of the second toothed wheel 24 is monitored by a second optical cell 54.

Figure 4:
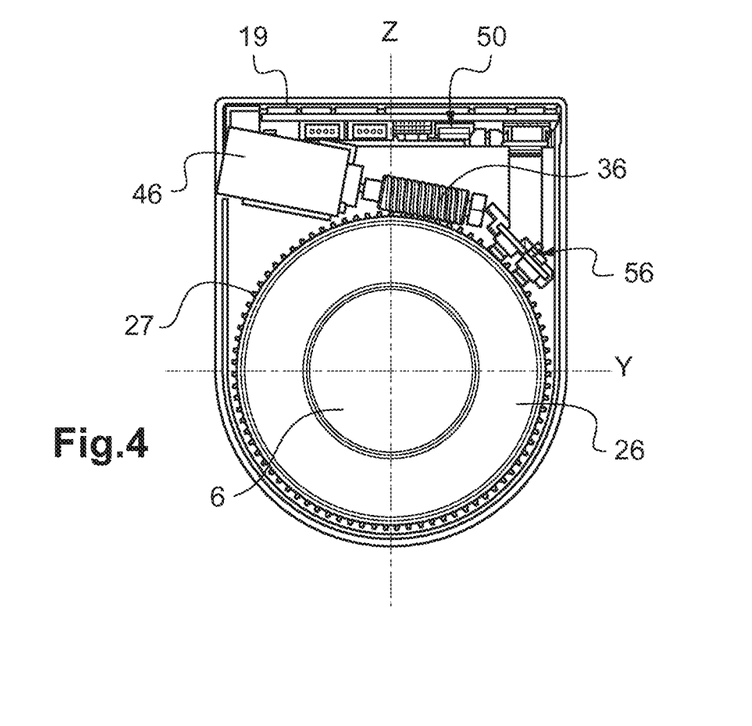
FIG. 4 shows a cutaway view of the vision compensating device in FIG. 2, on the variable spherical lens side.

As shown in FIG. 4, the third toothed wheel 27 is for its part rotated (about the optical axis X) by means of a third motor 46 that has a drive axis on which a third grub screw 36 that engages with the third toothed wheel 27 is mounted. The third motor 46 is for example mounted in the third portion 18 of the casing 12.

The current position of the third toothed wheel 27 is monitored by a third optical cell 56.

The first, second and third motors 42, 44, 46 are for example stepper motors having a resolution of 20 steps/turn, here set in 8ths of a step (referred to as micro-steps below). As a variant, these motors could be set in 16ths of a step.

The internal volume of the casing 12 (and moreover the internal volume of each of the first, second and third portions 14, 16, 18 in the same way) may be subdivided into a space for receiving the motors 42, 44, 46 (upper region of the casing 12 in the FIGS. 2, 3 and 4) and a space for receiving the optical elements 2, 4, 6 (lower region of the casing 12 in FIGS. 2, 3 and 4).

The space for receiving the motors 42, 44, 46 has an essentially parallelepipedal shape open (toward the bottom in the figures) in the direction of the space for receiving the optical elements 2, 4, 6 and closed at the opposite end (toward the top in the figures) by an upper face 19 of the casing 12 (the upper face 19 of the casing 12 being formed by the assembled upper faces of the first, second and third portions 14, 16, 18 of the casing 12, respectively).

The arrangement of the motors 42, 44 and 46 is such as to advantageously make it possible to use a circular geometry over 180°, said circular geometry being centred on the optical axis as close as possible to the useful radius of the lenses.

The space for receiving the optical elements 2, 4, 6 has, in contrast to the space for receiving the motors, a cylindrical shape (bounded by the walls of the casing 12) that matches that of the third toothed wheel 27 over half the circumference of the latter.

In other words, the casing 12 (and therefore each of the first, second and third portions 14, 16, 18 of the casing 12) has, in the space for receiving the optical elements 2, 4, 6, a cylindrical shape with a diameter (perpendicular to the optical axis X) that is about the same as, and slightly larger than, that of the third toothed wheel 27.

The respective diameters of the toothed wheels 22, 24, 27 are chosen so as to preserve field despite the thickness of the optical subassembly.

The first motor 42 and the first grub screw 32 extend in the casing 12 in a direction Z perpendicular to the upper face of the casing 12 (and therefore especially perpendicular to the optical axis X) in such a way that the first motor 42 is housed in the space for receiving the motors whereas the first grub screw 32 lies in the space for receiving the optical elements.

As for the second motor 44 and the second grub screw 34, they extend in the casing 12 in the same direction, but opposite the first motor 42 and the first grub screw 34 relative to the cylindrical power lenses 2, 4. The second motor 44 is housed in the space for receiving the motors whereas the second grub screw 34 lies in the space for receiving the optical elements.

Thus, it will be noted that the first grub screw 32 and the second grub screw 34 are located on either side of the assembly formed by the first toothed wheel 22 and the second toothed wheel 24, and that the lateral bulk (along an axis Y perpendicular to the aforementioned axes X and Z) of these various parts (first grub screw 32, second grub screw 34, first or second toothed wheel 22, 24) is smaller than the diameter of the third toothed wheel 27 so that the first and second grub screws 32, 34 are contained in the space for receiving the optical elements without extra room being required to receive them.

Moreover, the first and second motors 42, 44 each have a bulk along the optical axis X larger than that of each of the first and second toothed wheels 22, 24, and even larger than that of each of the first and second portions 14, 16 of the casing 12. However, because these first and second motors 42, 44 are placed as indicated above on each side of the casing 12 (relative to the axis Z), they may each occupy a space that extends, along the optical axis X, in line with the first portion 14 and the second portion 16 of the casing 12.

For example, each of the first and second motors 42, 44 has a lateral bulk (outside diameter of the motor) comprised between 6 and 12, for example 10 mm, whereas the first and second toothed wheels 22, 24 each have a thickness (bulk along the axis X) comprised between 1 and 4, for example 2.5 mm.

The third motor 46 and the third grub screw 36 are in contrast located in the space for receiving the motors, in the region that extends along the axis X in line with the third portion 18 of the casing 12. Thus, the third grub screw 36 engages with the third toothed wheel 27 in an upper portion of the latter, thereby making it possible for the casing 12 to follow closely the shape of the casing 12 in the lower portion of the third toothed wheel 27, as indicated above.

In the example described, as shown in FIG. 4, the axis of the third motor 46 and the third grub screw 36 is slightly inclined relative to the upper face of the casing 12 (specifically relative to the aforementioned axis Y).

Provision may for example be made for the thickness of the third toothed wheel 27 to be comprised between 0.3 mm and 2 mm.

This arrangement of the various elements allows a relatively thin casing to be obtained, typically having a thickness comprised between 15 and 20 mm.

The casing 12 also comprises, for example in the upper region of the space for receiving the motors, a control element 50, here formed of a plurality of integrated circuits borne by a common printed circuit board.

Moreover a device for storing electrical power, here a battery 58 (though, as a variant, it could be a supercapacitor), is provided in order to make the apparatus standalone. Provision may for example also be made for contactless elements for recharging the power storing device 58. The battery 58 especially allows the motors 42, 44, 46 and the control element 50 to be supplied with electrical power.

In this respect, the control and command elements will be selected preferably for their low consumption.

The main elements of such a control element 50, and their connections to the aforementioned motors 42, 44, 46 and to the aforementioned optical cells 52, 54, 56, are schematically shown in FIG. 5.

The control element 50 comprises a receiving module 60 designed to receive, here via a wireless link, setpoint information, i.e. information indicating the values desired by the user for the spherical power S, the cylindrical power C and the angle of astigmatism α that define the compensation generated by the optical subassembly formed from the optical elements 2, 4, 6.

The receiving module 60 is for example an infrared receiving module that receives this setpoint information from an infrared emitting remote control controlled by the user. As a variant, provision could be made for this setpoint information to be received from a personal computer via a wireless link, for example a local wireless network; the user could in this case choose values of spherical power S, cylindrical power C and angle of astigmatism α for the vision compensating device by interactive selection on the computer.

The receiving module 60 transmits the setpoint information S, C, α received to a computing machine 66 (for example consisting of a processor executing a computer program so as to perform the functions of the computing machine, as described below), specifically to a computational module 68 controlled by this computing machine 66.

The computational module 68 computes the values of the angles $\alpha_1$, $\alpha_2$ and the value of the spherical power $S_V$ required in order to obtain the setpoint values S, C, α received as input, using the formulae given above. In the case where the planar-cylindrical lenses 2 and 4 have a cylindrical power of $-C_0$ and $C_0$, respectively, the following formulae will for example be used:

$$\begin{cases} \alpha_1 = \alpha - \frac{1}{2}\arcsin\left(\frac{C}{2C_0}\right) + \frac{\pi}{4} \\ \alpha_2 = \alpha + \frac{1}{2}\arcsin\left(\frac{C}{2C_0}\right) + \frac{\pi}{4} \end{cases}$$

$$S_V = S + \frac{C}{2}$$

The computing machine 66 also comprises a control module 70 that receives as input the values of the angles $\alpha_1$, $\alpha_2$ and spherical power $S_V$ calculated by the computational module 68 and emits control signals to the motors 42, 44, 46, in order to control each of the motors 42, 44, 46 independently of the others and obtain respective positions for the toothed wheels 22, 24, 27 that allow the desired values to be obtained:

the control module 70 controls the first motor 42 so as to make the first toothed wheel 22 turn about the optical axis X as far as the position in which the axis $Y_1$ of the optically active cylindrical surface of the convex planar-cylindrical lens 2 (borne by the first toothed wheel 22) makes an angle $\alpha_1$ with the reference direction $Y_0$;

the control module 70 controls the second motor 44 so as to make the second toothed wheel 24 turn about the optical axis X as far as the position in which the axis $Y_2$ of the optically active cylindrical surface of the concave planar-cylindrical lens 4 (borne by the second toothed wheel 24) makes an angle $\alpha_2$ with the reference direction $Y_0$; and the control module 70 controls the third motor 46 so as to make the third toothed wheel 27 turn about the optical axis X as far as the position in which the control ring of the variable spherical power sets the spherical power $S_V$ to the power calculated by the computational module 68.

The position of each toothed wheel 22, 24, 27 is known at each instant by virtue of the optical cells 52, 54, 56, respectively, which each measure, on the toothed wheel with which each is associated, the number of teeth that have passed through the optical cell relative to a reference point on the circumference of the wheel in question (for example a point devoid of teeth).

In the example described here, the first motor 42/first grub screw 32/first toothed wheel 22 assembly, just like the second motor 44/second grub screw 34/second toothed wheel 24 assembly, has a gear ratio such that one turn of the toothed wheel 22, 24 corresponds to 15040 micro-steps of the associated motor 42, 44. The resolution (angle of rotation of the toothed wheels 22, 24 for one micro-step) is therefore 0.024° for the angles $\alpha_1$ and $\alpha_2$.

The third motor 46/third grub screw 36/third toothed wheel 46 assembly for its part has a gear ratio of 16640 micro-steps per turn. The ring for controlling the variable spherical power is adjustable over an angular span of 120° (therefore corresponding to 5547 micro-steps) so as to obtain the variation in spherical power from −25 D to 25 D (i.e. a span of variation of 50 D). The resolution (variation in spherical power $S_V$ per micro-step) is therefore 0.009 D.

Provision may be made, during passage from initial setpoint values $\alpha_1$, $\alpha_2$, $S_V$ to new setpoint values $\alpha'_1$, $\alpha'_2$, $S'_V$, for each of the first, second and third motors 42, 44, 46 to be actuated for a given length of time T (in seconds) that may optionally depend on the amplitude of one of the setpoint changes (for example on the variation, in absolute value, in spherical power $|S'_V - S_V|$, where $|x|$ is the absolute value of x).

To do this, the computing machine 66 for example determines the number $p_1$ of micro-steps of the motor 42 allowing passage from the angle $\alpha_1$ to the angle $\alpha'_1$, the number $p_2$ of micro-steps of the motor 44 allowing passage from the angle $\alpha_2$ to the angle $\alpha'_2$ and the number $p_3$ of micro-steps of the motor 46 allowing passage from the spherical power $S_V$ to the spherical power $S'_V$. The computing machine 66 then commands the motor 42 to rotate at a speed of $p_1/T$ micro-steps per second, the motor 44 to rotate at a speed of $p_2/T$ micro-steps per second and the motor 46 to rotate at a speed of $p_3/T$ micro-steps per second.

The control element 50 also comprises a temperature sensor 62, which delivers information on measured ambient temperature, and an inclinometer 64, for example taking the form of an accelerometer, which delivers information on the orientation of the vision compensating device 10, for example relative to the vertical. In the application described hereinafter with reference to FIGS. 6 to 8, the item of orientation information can be used to determine the position of the vision compensating device, and consequently which eye is corrected by this vision compensating device, and/or the inclination of the vision compensating device with respect to the vertical so as to determine whether the user's gaze is with regard to far vision, intermediate vision or near vision.

The computing machine 66 receives the item of temperature information generated by the temperature sensor 62 and the item of orientation information generated by the inclinometer 64 and uses at least one of these pieces of information in the context of the determination of the commands to send to the motors 42, 44, 46.

In the example described, the control module 70 uses the item of temperature information in order to compensate for variations in the spherical power of the lens 6 due to temperature (about 0.06 D/° C. in the described example) and the item of orientation information in order to compensate for possible disturbances of the drive system (motors, grub screws, toothed wheels) due to changes in the orientation of the vision compensating device 10.

In contradistinction to the case of the description of FIGS. 2 to 4 hereinabove, the description which follows of FIGS. 6 and 7 makes reference to directions (horizontal and vertical particularly) and to relative positionings ("lower" or "upper") which correspond to the use of the vision compensating spectacles (here trial spectacles) for measuring the visual acuity of the wearer.

Figure 6:
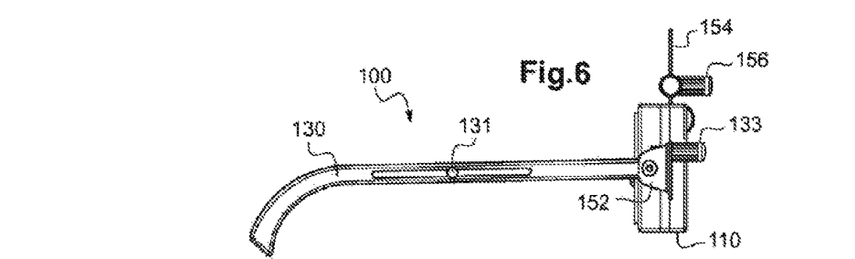
FIG. 6 represents in a side view a pair of trial spectacles using two vision compensating devices of the type of that represented in FIGS. 2 to 4.
Figure 7:
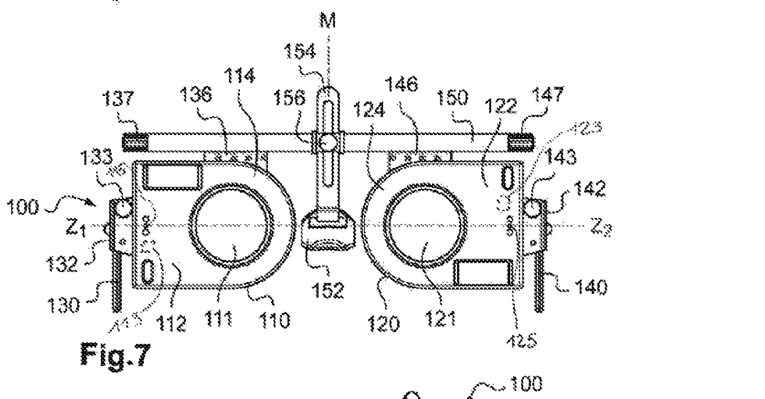
FIG. 7 represents in an end-on view the pair of trial spectacles of FIG. 6.

FIGS. 6 and 7 represent, respectively in a side view and in an end-on view, a pair of trial spectacles using two vision compensating devices 110, 120 of the type which has just been described with reference to FIGS. 1 to 5.

The two vision compensating devices 110, 120 are here identical but mounted on support means on a wearer's face, as explained in greater detail hereinbelow, so as to be disposed symmetrically with respect to a median vertical plane M which corresponds to the wearer's sagittal plane.

Specifically, the vision compensating device 110 intended for the wearer's right eye is disposed such that its space (here parallelepipedal) for receiving the motors 112 is situated laterally and towards the exterior (that is to say on the right viewed from the wearer) of its space (here cylindrical) for receiving the optical elements 114 (that is to say the eyepiece 111 of the vision compensating device 110).

Stated otherwise, the axis $Z_1$ of the vision compensating device 110 (which corresponds to the axis Z of FIGS. 2 to 4 for the vision compensating device 110) is perpendicular to the median plane M (wearer's sagittal plane) and the space for receiving the optical elements 114 (or the eyepiece 111) is situated between the space for receiving the motors 112 and the median plane M.

Likewise, the vision compensating device 120 intended for the wearer's left eye is disposed such that its space (here parallelepipedal) for receiving the motors 122 is situated laterally and towards the exterior (that is to say on the left viewed from the wearer) of its space (here cylindrical) for receiving the optical elements 124 (that is to say the eyepiece 121 of the vision compensating device 120).

Stated otherwise, the axis $Z_2$ of the vision compensating device 120 (which corresponds to the axis Z of FIGS. 2 to 4 for the vision compensating device 120) is perpendicular to the median plane M (wearer's sagittal plane) and the space for receiving the optical elements 124 (or the eyepiece 121) is situated between the space for receiving the motors 122 and the median plane M.

The pair of trial spectacles 100 comprises two branches 130, 140 mounted respectively on the vision compensating device 110 and on the vision compensating device 120, each time on a lateral end face of the vision compensating device 110, 120 concerned and by means of a lateral fastener 132, 142.

Each branch 130, 140 comprises a bent portion (for positioning the wearer's ear) at its opposite end from the vision compensating device 110, 120 concerned. Each branch 130, 140 is furthermore adjustable in length by means of a suitable adjustment system 131 (for example a possibility of sliding between two half-branches forming the branch 130, 140 concerned) so as to be able to tailor the distance between the patient's eyes and the vision compensating devices 110, 120.

Each branch 130, 140 is mounted on the corresponding lateral fastener 132, 142 with a possibility of rotational adjustment about a horizontal axis (parallel to the axis $Z_1$, $Z_2$ defined hereinabove) for example by means of a thumbwheel 133, 143 so as to be able to tailor the pantoscopic angle.

As already indicated, the lateral fastener 132, 142 is fixed on the lateral end wall (referenced 19 in FIGS. 3 and 4) of the vision compensating device concerned 110, 120 (that is to say, for the lateral fastener 132, on the right of the vision compensating device 110 intended for the wearer's right eye and, for the lateral fastener 142, on the left of the vision compensating device 120 intended for the wearer's left eye). On each side, the space for receiving the motors 112, 122 is therefore situated between the lateral fastener 132, 142 and the space for receiving the optical elements 114, 124 (or the eyepiece 111, 121).

The vision compensating devices 110, 120 are both mounted on a crosspiece 150 forming a frame element, on either side of the median plane M, respectively by means of a first slider 136 and of a second slider 146.

The position of each of the first and second sliders 136, 146 is adjustable in translation along the direction of extension of the crosspiece 150 (for example by means of a thumbwheel 137, 147 provided for this purpose), thereby allowing adjustment in a horizontal direction perpendicular to the median plane M (that is to say to the wearer's sagittal plane) of the position of each vision compensating device 110, 120. It is thus possible to adapt (independently of one another) the respective positions of the vision compensating devices 110, 120 to suit the semi-pupillary distances on the wearer's right side and left side.

A nasal support 152 (designed to press on the upper portion of the wearer's nose) is mounted on the crosspiece 150, in the middle of the latter (that is to say at the level of the median plane M), by way of a central fastener 154 provided with an oblong opening which receives a peg secured to the crosspiece 150 so as to allow adjustment in a vertical direction of the relative position of the nasal support 152 and of the crosspiece 150. This adjustment is performed for example by means of a thumbwheel 156 provided for this purpose.

Provision may be made furthermore for a possibility of rotation of the central fastener 154 about the horizontal axis of extension of the crosspiece 150 so as to adjust the position of the nasal support 152 depth-wise (that is to say along the optical axis of the vision compensating devices 110, 120).

Figure 8:
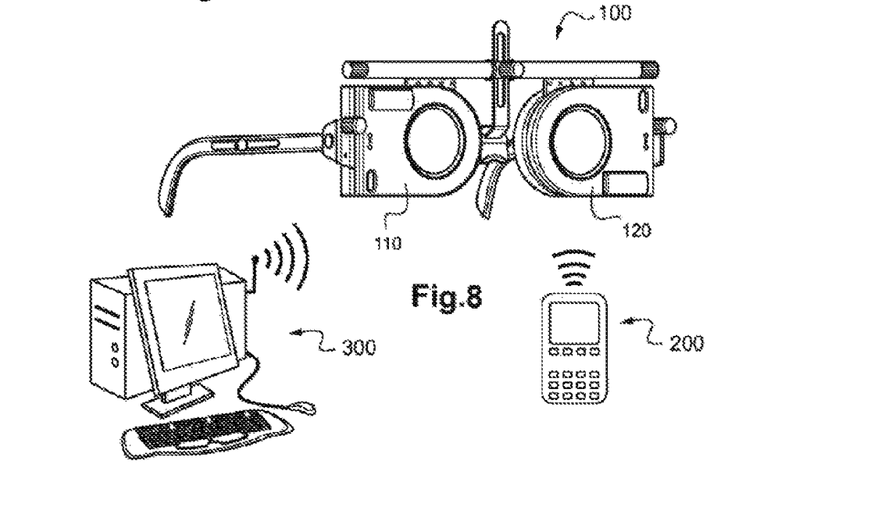
FIG. 8 presents a conventional example of use of the trial spectacles of FIGS. 6 and 7.

A conventional example of use of the trial spectacles 100 which have just been described is now described with reference to FIG. 8.

The trial spectacles 100 are placed on the patient's face, by tailoring the various adjustments described hereinabove to the morphology of the patient, in the rules of the art.

The visual examination can then begin.

The practitioner dispatches setpoints (information indicative of the values desired by the user for the spherical power S, the cylindrical power C and the angle of astigmatism $\alpha$) for the right eye and for the left eye by means of the wireless link mentioned hereinabove.

Accordingly, he uses for example as already indicated an infrared remote control 200 designed to dispatch data representative of the setpoints to the control elements 50 via the reception modules 60 implanted respectively in the vision compensating device 110 and in the vision compensating device 120. As already indicated, the practitioner could use as a variant a computer 300, designed for example to establish a wireless local area network with the reception modules 60 (which in this variant are radio reception modules).

Provision may also be made for the data representative of the setpoints to be emitted by an electronic apparatus that has performed an ametropia measurement on the patient. The trial spectacles 100 will in this case be used to validate the refraction resulting from the ametropia measurements.

It is proposed for example as already indicated that the electronic device of the practitioner (remote control, computer or ametropia measurement apparatus in the examples which have just been mentioned) emits data representative of the setpoints for both eyes and that the control element 50 embedded in each vision compensating device 110, 120 determines which setpoints are intended for it.

Accordingly, provision is made here for the control element 50 to determine, on the basis of the orientation information received from the accelerometer 64, what is the orientation of the vision compensating device 110, 120 concerned and consequently with which eye this vision compensating device 110, 120 is associated. Indeed, in the example described, the vision compensating devices 110, 120 are identical and are mounted symmetrically with respect to the median plane M, as already indicated.

As a variant, provision could be made for the control element 50 to store an item of information indicative of the position (on the right or on the left) of the vision compensating device 110, 120 concerned in the pair of trial spectacles 100.

Furthermore, for each eye and for each parameter (spherical power S, cylindrical power C and angle of astigmatism $\alpha$), provision may be made for several setpoint values to be transmitted to the vision compensating device 110, 120 concerned, the various values being associated with various angles of inclination of the device concerned with respect to the vertical, or with various angular spans of inclination of the device concerned with respect to the vertical, or else with various types of vision (far vision, intermediate vision, near vision).

For a vision compensating device, inclination with respect to the vertical (within the context of vision compensating spectacles such as those of FIGS. 6 and 7) is intended to mean the angle formed by the Y axis of FIGS. 3 and 4 with the vertical, which corresponds to the inclination with respect to the horizontal of the optical axis X of the vision compensating device.

When the wearer stands with their head straight and gazes into the far distance (far vision) this angle is zero or small (less than 10°); on the other hand, in near vision, this angle is conventionally 30°.

When a vision compensating device 110, 120 (and specifically its control element 50) receives various setpoint values (associated with various inclination values) for a parameter, it determines by means of the orientation information received from the accelerometer 64 the current inclination with respect to the vertical and controls the optical elements (as explained hereinabove with reference to FIG. 5) by using the values of the parameters associated with the inclination thus determined.

Concerning intermediate vision, provision may be made for the electronic device of the practitioner (remote control, computer) to emit specific values of the various parameters for an inclination span comprising the inclination of 20° (conventionally associated with intermediate vision), for example the span of values lying between 15° and 25°. As a variant, the control element 50 could calculate values of the various parameters for intermediate vision on the basis of corresponding values received for far vision and for near vision, and apply these calculated values when it determines, on the basis of the orientation information received from the accelerometer 64, that the current inclination lies in the aforementioned span.

According to a possibility of embodiment, provision may be made, for example in each vision compensating device 110, 120, for a telemeter 113, 123 designed to measure the distance of the object observed in the direction of gaze (for example by means of an ultrasound system or by triangulation). The control element 50 can then adapt the spherical power as a function of the distance of the observed object, for example by increasing the spherical power when the object is close so as to compensate a defect of visual accommodation.

The product is a not particularly fragile item of optics equipment, but having regard to its portability it is possible to provide a base to ensure the contactless recharging of the two vision compensating devices 110, 120 and/or verify its calibration by using an instrument of focimeter type, so as to guarantee the level of result desired.

It is understood from the foregoing description that the trial spectacles described hereinabove will be able to be used for purposes of subjective refraction, whether it be for far vision, intermediate vision or near vision.

These trial spectacles exhibit with respect to traditional trial spectacles the benefit of very great reactivity, of not having to remove the spectacles from the wearer's head in order to modify the correction thereof, and of offering an alterable correction value as a function of the inclination of the head.

Provision may also be made to use such spectacles in controlled conditions of field of vision, on the basis of a screen presenting mobile stimuli; the accelerometers fitted to the vision compensating devices will then make it possible to record the patient's head movements necessary for tracking the target.

It will therefore be possible by subtraction of the movements of the head with respect to the theoretical movement that would have been caused by the target to deduce therefrom the intrinsic movement of the eyes.

In order to carry out a monocular refraction, an occluding device, not represented, will be able to be placed on the optical window of one of the eyepieces 111, 121. As an alternative, the automation of the device will make it possible to carry out this right/left separation allowing monocular refraction by means of a blurring on the eye to be occluded by adding a predetermined optical power (for example of a value of about one dioptre).

According to another conceivable use, the vision compensating spectacles proposed hereinabove will be able to be used in the guise of test mounting making it possible for example to reproduce the future correction under the actual conditions of use, for example for a demonstration of the use of mid-distance progressive lenses.

In this context, provision may be made furthermore for an additional button 115, 125 on an exterior face of the vision compensating devices 110, 120 which allows, when it is depressed, a predetermined modification of the value of a correction parameter (spherical power S, cylindrical power C or angle of astigmatism α).

The wearer of the trial spectacles can thus obtain (for example by means of several presses of the button) an adjustment which is more appropriate for him or her.

The invention claimed is:

1. Vision-compensating spectacles comprising:
    a support system configured to provide support on a wearer's face;
    at least one optical subassembly mounted on the support system opposite at least one of the wearer's eyes, the optical subassembly comprising
        three optical elements mounted on the support system in series along an optical axis, the three optical elements including
            a first optical element of cylindrical power for a direction of gaze of the wearer along the optical axis,
            a second optical element of cylindrical power for the direction of gaze, and
            a third optical element of variable spherical power for the direction of gaze,
            the first optical element and the second optical element being adjustable in rotation about the optical axis independently of one another; and
        an energy storage system configured to energize an adjustment system to adjust the position of the first optical element about the optical axis, and the position of the second optical element about the optical axis, the adjustment system being configured to drive a ring to rotate to adjust the spherical power of the third optical element.

2. The spectacles according to claim 1, wherein the optical axis is perpendicular to the cylinder axis of the first and second optical elements.

3. The spectacles according to claim 1, wherein the optical subassembly comprises an electronic card configured to control the spherical power of the third optical element, the position of the first optical element about the optical axis, and the position of the second optical element in rotation about the optical axis as a function of setpoint information.

4. The spectacles according to claim 3, wherein the optical subassembly comprises an inclinometer, and
    the electronic card is configured to determine the setpoint information as a function of an item of inclination information received from the inclinometer.

5. A method of subjective refraction of an individual wearing spectacles according to claim 4, the method comprising:
    determining a type of vision by using the inclinometer;
    determining, by the electronic card, at least one item of setpoint information associated with the determined type of vision; and
    tailoring the optical power of the third optical element, the position of the first optical element, or the position of the second optical element as a function of the determined item of setpoint information.

6. The spectacles according to claim 3, wherein the optical subassembly comprises a telemeter, and
    the electronic card is configured to determine the setpoint information as a function of an item of distance information received from the telemeter.

7. A method of subjective refraction of an individual wearing spectacles according to claim 6, the method comprising:
    determining a type of vision by using the inclinometer;
    determining, by the electronic card, at least one item of setpoint information associated with the determined type of vision; and
    tailoring the optical power of the third optical element, the position of the first optical element, or the position of the second optical element as a function of the determined item of setpoint information.

8. The spectacles according to claim 3, further comprising a button actuatable by the wearer, wherein the electronic card is configured to modify the spherical power of the third optical element when the button is pressed.

9. A method of subjective refraction of an individual wearing spectacles according to claim 8, the method comprising:
detecting the pressing of the button; and
tailoring the optical power as a function of data received from the electronic card.

10. The spectacles according to claim 1, wherein the optical subassembly is mounted on a frame element and is mounted adjustable along a horizontal axis on the frame element.

11. The spectacles according to claim 1, wherein the optical subassembly is mounted on a frame element,
the support system comprises a nasal support, and
the nasal support is mounted adjustable on the frame element.

12. The spectacles according to claim 1, wherein the support system comprises a branch of adjustable length.

13. The spectacles according to claim 1, wherein the third optical element is a lens comprising a cavity closed by a deformable membrane and containing a liquid.

14. Vision-compensating spectacles comprising:
a support system configured to provide support on a wearer's face;
at least one optical subassembly mounted on the support system opposite at least one of the wearer's eyes, the optical subassembly comprising
three optical elements mounted on the support system in series along an optical axis, the three optical elements including
a first optical element of cylindrical power for a direction of gaze of the wearer along the optical axis,
a second optical element of cylindrical power for the direction of gaze, and
a third optical element of variable spherical power for the direction of gaze,
the first optical element and the second optical element being adjustable in rotation about the optical axis independently of one another;
a first motor configured to rotate the first optical element;
a second motor configured to rotate the second optical element;
a third motor configured to drive a ring to rotate to thereby adjust the spherical power of the third optical element; and
a battery supplying electrical power to the first motor, the second motor, and the third motor.

15. The spectacles according to claim 14, wherein the third optical element is a lens comprising a cavity closed by a deformable membrane and containing a liquid.

* * * * *